(12) United States Patent
Melzig et al.

(10) Patent No.: US 7,544,315 B2
(45) Date of Patent: Jun. 9, 2009

(54) PHOTOCHROMIC H-ANNELLATED BENZO[F]CHROMENE COMPOUNDS

(75) Inventors: Manfred Melzig, Wessling (DE); Yven Rohlfing, Munich (DE); Udo Weigand, Munich (DE)

(73) Assignee: Rodenstock GmbH, Munich (DE)

( * ) Notice: Subject to any disclaimer, the term of this patent is extended or adjusted under 35 U.S.C. 154(b) by 0 days.

(21) Appl. No.: 11/785,899

(22) Filed: Apr. 20, 2007

(65) Prior Publication Data

US 2007/0246692 A1    Oct. 25, 2007

Related U.S. Application Data

(63) Continuation of application No. PCT/EP2005/011202, filed on Oct. 18, 2005.

(30) Foreign Application Priority Data

Oct. 21, 2004 (DE) .................... 10 2004 051 509

(51) Int. Cl.
G02B 5/23 (2006.01)

(52) U.S. Cl. .................. 252/586; 544/111; 544/150; 546/196

(58) Field of Classification Search ............. 252/586; 544/111, 150; 546/196
See application file for complete search history.

(56) References Cited

U.S. PATENT DOCUMENTS

| | | | |
|---|---|---|---|
| 3,567,605 A | 3/1971 | Becker | |
| 4,826,977 A | 5/1989 | Heller et al. | |
| 4,931,220 A | 6/1990 | Haynes et al. | |
| 5,244,602 A | 9/1993 | Van Gemert | |
| 5,427,774 A | 6/1995 | Chaudhuri et al. | |
| 5,552,090 A | 9/1996 | Van Gemert et al. | |
| 5,552,091 A | 9/1996 | Kumar | |
| 5,585,042 A | 12/1996 | Knowles | |
| 5,698,141 A | 12/1997 | Kumar | |
| 5,723,072 A | 3/1998 | Kumar | |
| 5,869,658 A | 2/1999 | Lin et al. | |
| 6,022,495 A * | 2/2000 | Kumar | 252/586 |
| 6,146,554 A | 11/2000 | Melzig et al. | |
| 6,225,466 B1 | 5/2001 | Mann et al. | |
| 6,306,316 B1 | 10/2001 | Mann et al. | |
| 6,331,625 B1 | 12/2001 | Mann et al. | |
| 6,340,765 B1 | 1/2002 | Momoda et al. | |
| 6,686,468 B2 * | 2/2004 | Mann et al. | 544/150 |
| 6,719,926 B2 | 4/2004 | Momoda et al. | |
| 2006/0226402 A1 * | 10/2006 | Kim et al. | 252/586 |

FOREIGN PATENT DOCUMENTS

| | | |
|---|---|---|
| EP | 0 600 688 B1 | 6/1994 |
| EP | 0 691 965 B1 | 1/1996 |
| EP | 1 230 234 B1 | 8/2002 |
| EP | 1 248 778 B1 | 10/2002 |
| WO | WO 97/20239 A1 | 6/1997 |
| WO | WO 99/15518 A1 | 4/1999 |
| WO | WO 01/36406 A1 | 5/2001 |
| WO | WO 02/22594 A1 * | 3/2002 |

OTHER PUBLICATIONS

International Search report dated Feb. 20, 2006 with English translation of relevant portion (Five (5) pages).
International Preliminary Report on Patentability dated May 3, 2007, and PCT/ISA/237 with English translation (Written Opinion of the International Searching Authority) (six (6) pages).

* cited by examiner

*Primary Examiner*—Ling-Siu Choi
*Assistant Examiner*—Bijan Ahvazi
(74) *Attorney, Agent, or Firm*—Crowell & Moring LLP

(57) ABSTRACT

Photochromic h-annellated benzo[f]chromene compounds, especially photochromic compounds derived from benzo[f] chromenes, which compounds have particular long wavelength absorption maxima in their closed form and exhibit good performance in the open, colored form, so that good compatibility is achieved with indenonaphthopyrans which are diffused in phototropic glasses used in phototropic glass applications, and the use of such photochromic h-annellated benzo[f]chromene compounds in photochromic synthetic resin articles, particularly ophthalmic lenses.

9 Claims, 1 Drawing Sheet

Reaction Scheme i) Addition/elimination of water (R* = carboxylic acid protective group, e.g., ortho ester)

ii) Hydrolysis of carboxylic acid protective group R* to -COOH iii) Intramolecular cyclization iv) Naphthopyran condensation ectrum of the visible light. We prefer that the spectrum absorption of the open form is in the range of about 400 nm to about 800 nm. Especially preferred is a spectrum absorption in the range of 420 nm to 700 nm, and still more preferred in the range of 450 nm to 650 nm.

PHOTOCHROMIC H-ANNELLATED BENZO[F]CHROMENE COMPOUNDS

CROSS REFERENCE TO RELATED APPLICATIONS

This application is a continuation of international patent application no. PCT/EP2005/011202, filed Oct. 18, 2005 designating the United States of America and published in German on May 4, 2006 as WO 2006/045495, the entire disclosure of which is incorporated herein by reference. Priority is claimed based on Federal Republic of Germany patent application no. DE 10 2004 051 509.3, filed Oct. 21, 2004.

BACKGROUND OF THE INVENTION

The present invention relates to specific photochromic h-fused or h-annellated benzo[f]chromene compounds and their use in plastics of all types, in particular for ophthalmic purposes. The present invention relates in particular to photochromic compounds derived from benzo[f]chromenes which in their closed form have especially long wavelength absorption maxima with good efficiency in the open colored form at the same time, so that when used in phototropic lenses, they are well compatible with the indenonaphthopyrans widely used therein.

Various classes of dyes are known which undergo reversible changes in color when exposed to light of certain wavelengths, in particular sunlight. This is due to the fact that these dye molecules change to an excited colored state by energy input in the form of light, then leave this state again when the energy input is interrupted and return to their colorless or at least almost colorless normal state. These photochromic dyes include for example the naphthopyrans which have already been described with various substituents in the prior art.

Pyrans, specifically naphthopyrans and larger ring systems derived therefrom, are photochromic compounds which even today are the subject of intense investigations. Although a patent application was filed for these compounds for the first time back in 1966 (U.S. Pat. No. 3,567,605), compounds that appeared to be suitable for use in eyeglass lenses were not developed until the 1990s.

The world market for photochromic eyeglasses made of silicate as well as plastic is dominated by the colors gray and brown. Colors such as green, blue, magenta, orange or yellow play a completely subordinate role.

In all photochromic plastic lenses currently on the market, these two colors are achieved by mixtures of at least two photochromic dyes. As explained in U.S. Pat. No. 6,306,3126 [sic] these may be divided into two groups, namely those whose longest wavelength absorption maximum is above 550 nm, i.e., those which in an excited state yield a violet blue to green transmission color and those whose longest wavelength absorption maximum is below 550 nm. Their transmission color ranges from yellow to orange to red.

The first group includes 2H-naphthopyrans derived from 1-naphthols and their higher analogs derived therefrom by fusion. These are described in U.S. Pat. No. 5,698,141, U.S. Pat. No. 5,723,072, U.S. Pat. No. 6,146,554, U.S. Pat. No. 6,225,466, U.S. Pat. No. 6,331,625 and U.S. Pat. No. 6,340,765, for example. Although photochromic compounds belonging to other classes, as described in U.S. Pat. No. 4,931,220 or EP 0 600 688, have absorption maxima above 550 nm, they are no longer in commercial use because of their short lifetime and/or short bandwidth of the long wavelength absorption. The long wavelength absorption of photochromic dyes of all gray or brown photochromic plastic lenses currently available on the market (e.g., Rodenstock Perfalit ColorMatic Extra®—since 1999, Transitions Next Generation®—since 2002, Hoya Solio® 1.55—since 2004) belong to the compounds derived from 1-naphthols described above.

Dyes belonging to the second group include mostly 3H-benzopyrans and 3H-naphthopyrans which are derived from 2-naphthols and are mostly substituted with aryl or heteroaryl in position 2, as described in U.S. Pat. No. 5,244,602, U.S. Pat. No. 5,427,774, U.S. Pat. No. 5,552,090, U.S. Pat. No. 5,552,091, U.S. Pat. No. 5,585,042 and WO 97/20239. The spiroadamantane-substituted compounds described in U.S. Pat. No. 4,826,977 also belong to this group. It is possible to use 2H-naphtho[1,2—b]pyrans derived from 1-naphthols only if the open form is sterically hindered by substitution in position 5 of the system, as described in EP 1 248 778. Without this hindrance, the brightening effect is too slow for use in eyeglass lenses.

Commercially available photochromic compounds such as Reversacol Sunflower, Corn Yellow, Flame and Ruby (James Robinson) or CNN-4 and CNN-8 (Tokuyama Soda) are described in EP 0 691 965 and U.S. Pat. No. 6,719,926. These compounds all have an amino group, usually piperidine or morpholine in position 6 of the naphthopyran system, yielding a very high molar extinction (IOD>1.5) in the absorption maximum. Without this functional group, the value is approximately 1.5 lower. Unfortunately, this strongly polar substitution pattern results in strong solvatochromism, so that a portion of the dye used is in the open form in the solid solution (plastic matrix). This is manifested even in the complete absence of exciting light in lightly colored lenses. In addition the transmission after $V_\lambda$ is also reduced by 4 to 10%. Examples that can be mentioned here include mainly the brown variants of Rodenstock ColorMatic Extras and Hoya Solio® 1.55.

Another disadvantage is the absorption of the closed form, which has a hipsochromic shift of 20 nm to 25 nm in comparison with the dyes of the first group. The composition is coordinated, i.e., the respective concentrations of the photochromic dyes used are coordinated to achieve a gray or brown color in such a way that the desired color is achieved in normal direct or indirect sunlight. If the very short wavelength portion of the visible sunlight (380-400 nm) is selectively filtered out or blocked, e.g., by window glass with a thermal insulation coating or laminated safety glass in motor vehicles, then the lenses assume a blue color in the case of a gray lens or a gray color in the case of a brown lens. This can be observed well in brightly lit rooms with the plastic photochromic lenses available on the market today and is a cosmetic disadvantage.

Compounds that have a longer wavelength absorption of the closed form due to their structure are described in WO 02/22594. However, the important aspect here is that powerful dyes which absorb in the long wavelength range, i.e., in the violet to blue range are provided, i.e., they have the longer wavelength absorption of the open form. This has been achieved by introducing amino substituents into the naphthopyran system. These compounds have the longest wavelength absorption maxima of the open form which are not below 540 nm. Here again, however, the precoloration when used in plastic eyeglass lens materials is a disadvantage.

U.S. Pat. No. 5,869,658 describes compounds having a similar basic structure, whose open form absorbs in the desired spectral range. However, this publication discusses only indeno-fused naphtho[2,1-b]pyrans, which are also substituted by an alkoxy group in position 6. This is obligatory due to the synthesis because the ring closure does not take place without an activating substituent that makes the linkage point in p-position nucleophilic. Fused ring systems larger than the five-membered ring are neither described nor possible by this route. Furthermore, the brightening rates are very high. For light exposure in equilibrium, this leads to only a small amount of open, i.e., colored, molecules. The darkening effect is minor (ΔOD<0.5). Likewise, the absorption of the closed form, usually with maxima below 370 nm, is at a much shorter wavelength than that of the compounds of the first group. However, this is not enough to utilize the long wavelength UV portion of sunlight. The dye molecules disclosed in U.S. Pat. No. 5,869,658 are relatively planar because the repulsion of the H atoms (in positions 8 and 9 of the formula in column 21) is not very great. Example 3 is unusual because in this case the slow brightening and thus greater darkening ΔOD are achieved due to a fluorine substituent in position 2 on phenyl rings B and/or B'. This effect, which makes the ΔOD value approximately four times greater, was already described in U.S. Pat. No. 5,066,818. However, this substitution which hinders the free rotation leads to an undesirably strong dependence of the brightening on the matrix surrounding the molecule, i.e., a very broad distribution of the brightening rate when the molecular ensemble in a matrix is considered and/or an extremely different brightening rate in different plastic materials.

EP 1,230,234 also describes 2H-diarylnaphthopyrans substituted with condensed rings. Condensation within the indene ring in the structure shown here leads to compounds which usually brighten as quickly as the comparative compound C5 owing to the absence of steric hindrance between the $CH_2$ group of the five-membered ring and the H atom in position 8. As described in U.S. Pat. No. 3,567,605, compounds having this structure have adequate photochromicity only at extremely low temperatures. With the six-membered ring, the hindrance is also very minor, the brightening is quick and thus the observed coloration is only minor. In addition, the choice of possible compounds is very small and the synthesis described allows only compounds substituted in positions 6 and 7 with activating groups. When using only one methoxy group or using less activating higher alkoxy groups, no ring closure reaction takes place. Larger alkane rings are possible through synthesis but the steric hindrance is always low in comparison with that of compounds of the structure according to U.S. Pat. No. 5,869,658 or WO 02/22594; likewise the darkening results are minor. The essential aspect of these compounds according to EP 1,230,234, however, was primarily providing intrinsically gray or brown compounds. In the open form, the (substituted) phenyl group is in meta-position to the ethylene bridge instead of being in para-position, which leads to completely different behavior which is even controversial in some cases.

SUMMARY OF THE INVENTION

Thus the object of the present invention is to provide novel photochromic dyes which have improved properties in comparison with the compounds available in the prior art. These photochromic compounds should be characterized, compared to comparable compounds of the prior art, particularly by a longer wavelength absorption in the unexcited state, i.e., in the range between approximately 380 nm and 400 nm while at the same time having a good efficiency in the open form, i.e., characterized by a higher molar extinction of the excited form after exposure to light and by good kinetic properties and lifetime properties, i.e., with a rapid brightening rate which is adapted to the compounds that absorb in the long wavelength range and are usually used at the same time in phototropic lenses and with good results in the lifetime test.

These and other objects are achieved by the invention as described hereinafter.

In particular, photochromic h-fused benzo[f]chromenes corresponding to formula (I) are provided:

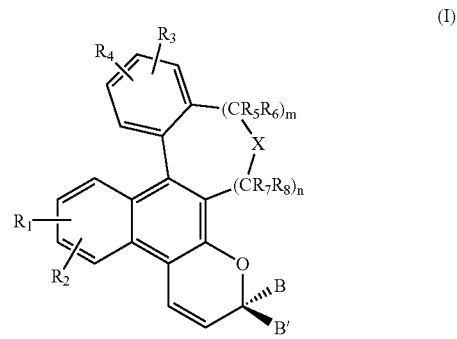

wherein
n and m independently of one another denote 0, 1 or 2,
$R_1$, $R_2$, $R_3$ and $R_4$ each independently of one another denote a substituent selected from
  the group α, consisting of a hydrogen atom, a ($C_1$-$C_6$) alkyl radical, a ($C_1$-$C_6$) thioalkyl radical, a ($C_3$-$C_7$) cycloalkyl radical, which may have one or more heteroatoms such as O or S, for example, a ($C_1$-$C_6$) alkoxy radical, a hydroxyl group, a trifluoromethyl group, bromine, chlorine and fluorine;
  the group β, consisting of an unsubstituted, a monosubstituted or disubstituted phenyl, phenoxy, benzyl, benzyloxy, naphthyl or naphthoxy radical, where the substituents may be selected from phenyl and the group α;
  the group γ, wherein the radicals $R_1$ and $R_2$ and/or $R_3$ and $R_4$ each denote an -A-$(CH_2)_k$-D- group or an -A-(C$(CH_3)_2)_k$-D- group bound to the aromatic ring, where k=1 or 2, where A and D independently of one another are selected from oxygen, sulfur, $CH_2$, $C(CH_3)_2$ or $C(C_6H_5)_2$ and again a benzo ring may be fused to this -A-$(CH2)_k$-D- group;
$R_5$, $R_6$, $R_7$ and $R_8$ each independently of one another are selected from phenyl and the group α or $R_5$ and $R_6$ together with the $R_3$ group of the directly vicinal benzo ring form an unsubstituted, a monosubstituted or disubstituted benzo or pyrido ring fused thereto, its substituents being selected from phenyl and the group α or, if m and/or n denotes 2 the directly vicinal radicals $R_5$ and $R_6$ of two vicinal $CR_5R_6$ units and/or the directly vicinal radicals $R_7$ and $R_8$ of two vicinal $CR_7R_8$ units together form a fused, unsubstituted, monosubstituted or disubstituted benzo ring or pyrido ring, whose substituents may be selected from phenyl and the group α, or $R_5$ and $R_6$ and/or $R_7$ and $R_8$ together form a ($C_3$-$C_7$) cycloalkyl group, which may have one or more heteroatoms, e.g., oxygen or sulfur, with a benzo ring optionally being fused to this cycloalkyl group;
X is selected from O, S or $CR_9R_{10}$, wherein $R_9$ and $R_{10}$ independently of one another are selected from phenyl and the group α, or $R_9$ and $R_{10}$ together form a ($C_3$-$C_7$) cycloalkyl group which may have one or more heteroatoms such as oxygen or sulfur, or $R_9$ and $R_{10}$ together with $R_5$ and $R_6$ and/or $R_7$ and $R_8$ of a directly vicinal $CR_5R_6$ unit and/or $CR_7R_8$ unit may denote an unsubstituted, a monosubstituted or a disubstituted benzo or pyrido ring fused to the X—C($R_5R_6$) and/or X-C($R_7R_8$) bond, whose substituents may be selected from phenyl and the group α with the proviso that X may not be $CR_9R_{10}$ when both m and n are 0;

B and B' independently of one another are selected from one of the following groups a), b), c) or d), wherein B and B' a) are mono-, di- and trisubstituted aryl groups, where the aryl group is phenyl or naphthyl;

b) are unsubstituted, monosubstituted and disubstituted heteroaryl groups where the heteroaryl group is pyridyl, furanyl, benzofuran-2-yl, benzofuran-3-yl, dibenzofuranyl, thienyl, benzothien-2-yl, benzothien-3-yl or dibenzothienyl;

wherein the substituents of the aryl or heteroaryl groups in a) and b) are those selected from the groups α, β or γ or an unsubstituted, monosubstituted or disubstituted amino group, where the amine substituents may be selected from $(C_1-C_6)$ alkyl, $(C_3-C_7)$ cycloalkyl, an unsubstituted phenyl or benzyl group or a phenyl or benzyl group substituted with one or more substituents from the group α, an N-morpholine group, an N-thiomorpholine group, an N-piperidine group, an N-azacycloheptane group, an N-piperazine group, an N—(N'—($C_1$-$C_6$-alkyl)piperazine group, an N-pyrrolidine group, an N-imidazolidine group, an N-pyrazolidine group, an N-aziridine group, an N-azetidine group, an N-indoline group, an N-carbazole group, an N-phenothiazine group, an N-phenazine group, an N-phenoxazine group, an N-tetrahydroquinoline group or an N-tetrahydroisoquinoline group, wherein the substituents are preferably those from groups α and β;

c) are structural units having the following formulas (V) and (W)

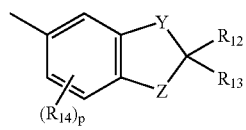

(V)

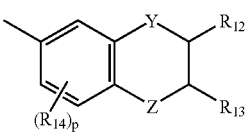

(W)

wherein

Y and Z independently of one another denote O, S, $CH_2$, $CMe_2$, NH, NPh or $N(C_1-C_6)$ alkyl, $R_{12}$ and $R_{13}$ independently of one another denote hydrogen or a $(C_1-C_6)$ alkyl radical, and $R_{14}$ denotes a substituent from the group α, where p is 1, 2 or 3, or d) B and B' together form an unsubstituted, monosubstituted or disubstituted 9,10-dihydroanthracene group, fluorene group, thioxanthene group or xanthen-9-ylidene group, benzo[b]fluoren-11-ylidene group, 5H-dibenzo[a,c]cycloheptene, dibenzosuberone or 5H-dibenzo[a,c]cyclooctan-5-ylidene group or a saturated hydrocarbon group which is $C_3$-$C_{12}$ spiromonocyclic, $C_7$-$C_{12}$ spirobicyclic and/or $C_7$-$C_{12}$ spirotricyclic, where the substituents on the unsaturated cyclic compounds are selected from the group α.

BRIEF DESCRIPTION OF THE DRAWING

The accompanying drawing FIGURE is a reaction scheme for preparing the compounds according to the invention.

DETAILED DESCRIPTION OF PREFERRED EMBODIMENTS

Figure 1:
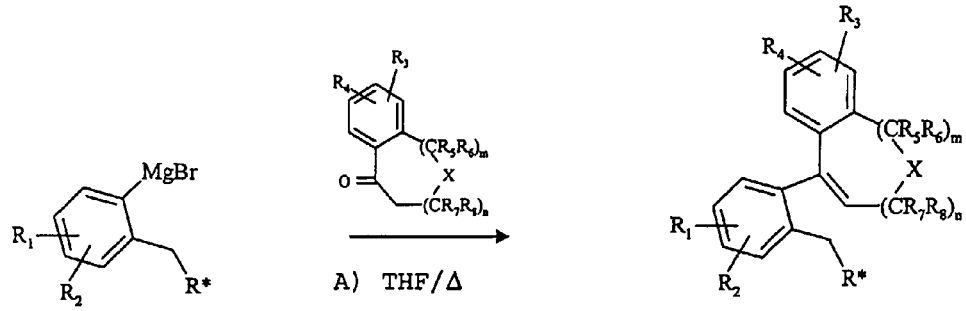
Figure 1:
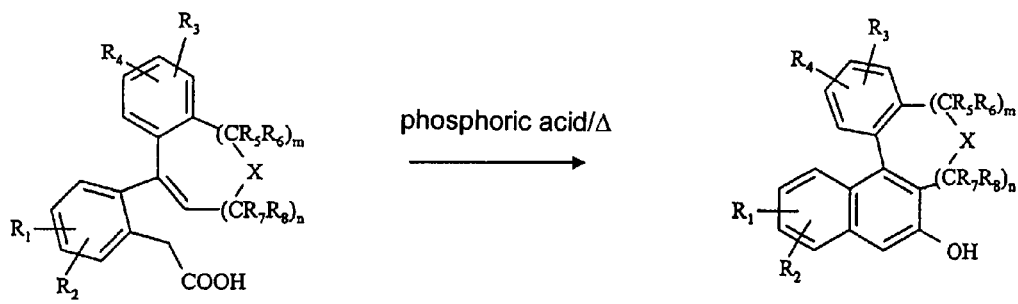
Figure 1:
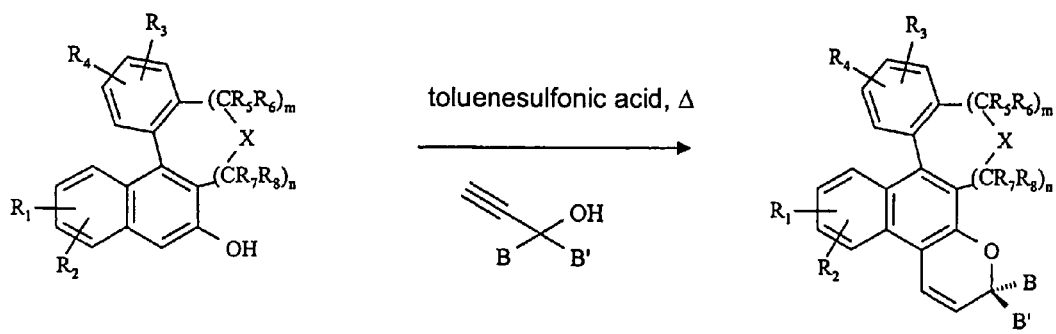

According to the present invention, compounds are provided by h-fusion of benzo[f]chromene systems such that their photochromic properties have important advantages in comparison with the compounds known in the art. In particular, the inventive compounds have long wavelength absorption maxima in the closed (colorless) form with at the same time a good efficiency in the open form, i.e., a higher molar extinction of the excited form on exposure to light as well as good kinetic properties and lifetime properties. Furthermore, the photochromic H-fused benzo[f]chromene compounds according to the invention have good service life properties comparable to those of the corresponding compounds known in the art and/or better kinetic properties, i.e., a rapid rate of brightening adapted to the photochromic dyes that today are usually used simultaneously in phototropic lenses and have a longer wavelength absorption as well as good behavior in the service life test.

The cyclic ring and/or heterocyclic ring fused in position h of the benzo[f]chromene system is preferably a five-membered ring (n=m=0; see formula (II) below), a six-membered ring (n=1, m=0 and m=1, n =0; see formula (III) below) or a seven-membered ring (preferably with n=m=1; see formula (IV) below).

The five-membered ring system having a $CH_2$ bridge is almost planar but is under a great deal of tension. With the standard molecular geometry program Hyperchem 7 (Monte Carlo, Mm+, 100 cycles), a value of −0.27° is obtained for the angle ε (rotation of the phenyl ring with respect to the plane of the naphthalene ring). The introduction of an oxygen atom relaxes the molecule by rotating the angle ε to −27.25°. Replacing the $CH_2$ bridge with a $CH_2$-$CH_2$ bridge to form a six-membered ring (ε=−25.39°) has the same effect. The seven-membered ring with a $CH_2$-$CH_2$-$CH_2$ bridge already yields a helicene-like structure (ε=−49.25°). The five-membered ring with O or S definitely has a stronger aromatic character than with a $CH_2$ or $CR_2$ group. This leads to a bathochromic shift of the absorption.

Preferred photochromic h-fused benzo[f]chromene compounds according to the present invention have the following general formulas (II), (III) and/or (IV):

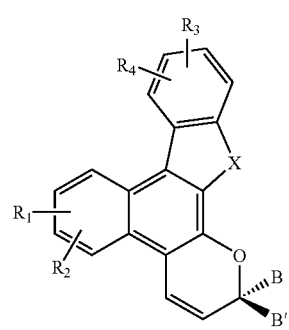

(II)

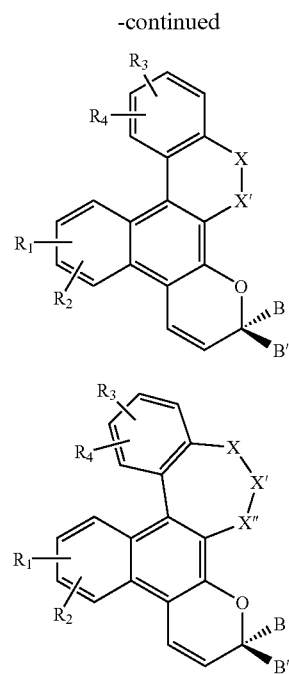

wherein B, B', $R_1$, $R_2$, $R_3$ and $R_4$ are defined as given above and in formula (II) X=O or S;

in formula (III) X and X' are independently selected from O, S and $CR_9R_{10}$, with the proviso that at least one of the two is $CR_9 R_{10}$; and/or in formula (IV) X, X' and X" are independently selected from O, S and $CR_9R_{10}$, with the proviso that when X' denotes O or S, then X and X" are each $CR_9R_{10}$.

$R_5$, $R_6$, $R_7$ and $R_8$ are preferably selected from the group α independently of one another. If in formulas (III) and/or (IV), X, X' and/or X" stands for $CR_9R_{10}$, then the radicals $R_9$ and $R_{10}$ together may stand for a $(C_1-C_6)$ alkyl radical or a $(C_3-C_7)$ cycloalkyl radical in particular which may have one or more heteroatoms.

$R_1$ and $R_2$ and/or $R_3$ and $R_4$ may each form an -A-(CH2)$_k$-D- group, where k=1 or 2, bound to the aromatic ring, where A and D, independently of one another, are selected from oxygen, sulfur, $CH_2$, $C(CH_3)_2$ or $C(C_6H_5)_2$ and where a benzo ring may in turn be fused to this -A-(CH2)$_k$-D- group; in particular —O—$(CH_2)_2$—O— may be listed as an -A-(CH2)$_k$-D- unit, with a benzocyclic ring optionally being fused to the ethylene group thereof. The -A-$(CH_2)_k$-D- unit is bound to the respective benzo ring by A and D in ortho position to one another.

In an especially preferred embodiment, B and B', independently of one another, in the formulas (I), (II) (III) and/or (IV) given above are mono-, di- or trisubstituted aryl groups, wherein the aryl group is a phenyl group or a naphthyl group.

Especially preferred photochromic h-fused benzo[f] chromene compounds according to the present invention include:

(1) 2-(4-methoxyphenyl)-2-phenyl-2H-benzofurano[1,2-h] benzo[f]-chromene,
(2) 2-(4-methoxyphenyl)-2-phenyl-2H-benzothiopheno[1,2-h]-benzo[f]chromene,
(3) 2-(4-methoxyphenyl)-2-phenyl-2H-13,14-dihydronaphtho-[1,2-h]benzo[f]chromene,
(4) 7-methoxy-2-(4-methoxyphenyl)-2-phenyl-2H-13,14-dihydro-naphtho[1,2-h]benzo[f]chromene,
(5) 11-methoxy-2-(4-methoxyphenyl)-2-phenyl-2H-13,14-dihydro-naphthp[1,2-h]benzo [f]chromene,
(6) 2-(4-methoxyphenyl)-2-phenyl-2H, 13H-chromeno[1,2-h]benzo-[f]chromene,
(7) 2-(4-methoxyphenyl)-2-phenyl-2H, 14H-chromeno [1,2-h]benzo-[f]chromene,
(8) 7-methoxy-2-(4-methoxyphenyl)-2-phenyl-2H-benzocycloheptano[1,2-h]benzo[f]chromene.

The longest wavelength absorption maxima $\lambda_{max}$ of the closed (colorless) form and the open (colored) form of different compounds are shown in the following table (the numbers are based on the list of especially preferred compounds). Furthermore, the efficiency of the colored form of the inventive compounds is also shown. To do so, 500 ppm photochromic dye was incorporated into a phototropic matrix of ColorMatic Extra® and after polymerization, the transmission was measured in a defined procedure on a kinetic bench at 23° C. (15 min exposure at 50 klux). The lower the transmission, the more intense is the power of the photochromic dye under exposure. However, it must also be pointed out that the transmission was measured as a factor weighted in relation to the optical sensitivity maximum $V_\lambda$ so that yellow-orange dyes whose absorption maximum is farther away from the human sensitivity maximum will have a higher transmission than orange red dyes whose absorption maximum is closer to the human sensitivity maximum. The intensity of two photochromic dyes can thus be compared well only by way of the degree of transmission under illumination if their longest wavelength absorption maxima (open form) are not too far apart (otherwise yellower dyes would be classified at a seemingly lower level than redder dyes). A compound of the prior art according to U.S. Pat. No. 5,869,658 is shown in the last row of the following table for comparison purposes.

The information given in the following table for m, n, X, $R_1$ and $R_3$ is based on the structure (I):

B is 4-methoxyphenyl
B' is phenyl
$R_2$=$R_4$=H

| No. | m $R_{5/6}$ | N $R_{7/8}$ | X | $R_1$ | $R_3$ | $\lambda_{max}$ (closed) | $\lambda_{max}$ (open) | Transmission darkened |
|---|---|---|---|---|---|---|---|---|
| (1) | 0 | 0 | O | H | H | 380 nm | 470 nm | 53% |
| (2) | 0 | 0 | S | H | H | 385 nm | 475 nm | 49% |
| (3) | 1 H/H | 0 — | $CH_2$ | H | H | 385 nm | 450 nm | 58% |
| (4) | 1 H/H | 0 — | $CH_2$ | 7-OMe | H | 400 nm | 470 nm | 40% |
| (5) | 1 H/H | 0 — | $CH_2$ | H | 11-OMe | 390 nm | 455 nm | 55% |

-continued

| No. | m | R$_{5/6}$ | N | R$_{7/8}$ | X | R$_1$ | R$_3$ | λ$_{max}$ (closed) | λ$_{max}$ (open) | Transmission darkened |
|---|---|---|---|---|---|---|---|---|---|---|
| (6) | 1 | H/H | 0 | — | O | H | H | 380 nm | 455 nm | 58% |
| (7) | 0 | — | 1 | H/H | O | H | H | 395 nm | 460 nm | 57% |
| (8) | 1 | H/H | 1 | H/H | CH$_2$ | 7-OMe | H | 380 nm | 485 nm | 40% |
| Prior Art | 0 | | 0 | | CH$_2$ | 6-OMe | H | 380 nm | 465 nm | 65% |

It can be seen from this table that the compounds according to the invention have a higher efficiency in the darkened state in comparison with the illustrative compound of the prior art. Furthermore, the absorption maximum of the closed form has a bathochromic shift in most cases. This property is especially important when only a small amount of UV radiation is available for excitation owing to scattering effects in the atmosphere. Longer wavelength UV radiation is subject to less scattering than shorter wavelength radiation, so these dyes undergo good darkening even under unfavorable conditions in contrast with photochromic dyes that absorb at a shorter wavelength.

The compounds according to the invention may be used in synthetic resin materials (i.e., plastics) and/or synthetic resin objects of all types and shapes for a variety of applications for which photochromic behavior is important. A dye according to the present invention or a mixture of such dyes may be used. For example, the photochromic benzo[f]chromene dyes according to the invention may be used in lenses, in particular ophthalmic lenses, lenses of eyeglasses of all types such as ski goggles, sunglasses, motorcycle goggles, visors of safety helmets and the like. Furthermore, the inventive photochromic benzo[f]chromene dyes may also be used as solar protection in vehicles and residences in the form of windows, safety visors, covers, roofs or the like.

For producing such photochromic objects, the photochromic benzo[f]chromene dyes according to the invention may be applied to or embedded in a polymer material such as an organic plastic material by means of various methods described in the prior art such as those described in WO 99/15518.

A distinction is made between so-called bulk or mass dyeing methods and superficial or surface dyeing methods. A bulk dyeing method comprises, for example, dissolving or dispersing the photochromic compound or compounds according to the present invention in a plastic material, e.g., by adding the photochromic compound(s) to a monomeric material before polymerization takes place. Another possibility for producing a photochromic object is by impregnating the plastic material(s) with the photochromic compound(s) by immersing the plastic material in a hot solution of the photochromic dye(s) according to the present invention or by a thermal transfer method, for example. The photochromic compound(s) may also be provided in the form of a separate layer between adjacent layers of the plastic material, e.g., as part of a polymer film. Furthermore, applying the photochromic compound(s) as part of a coating on the surface of the plastic material is also possible. The term impregnation should be understood to refer to the migration of the photochromic compound(s) into the plastic material, e.g., through the solvent-supported transfer of the photochromic compound(s) into a polymer matrix, vapor phase transfer or other such surface diffusion processes. Such photochromic objects, e.g., eyeglass lenses, can advantageously be produced not only by means of the usual bulk dyeing but also in the same way by means of surface dyeing; a surprisingly lower migration tendency can be achieved with the latter variant. This is advantageous in particular in the case of subsequent finishing steps, e.g., when an antireflective coating is applied due to the lower backdiffusion in vacuo—drastically reducing layer separation and similar defects.

Thus on the whole, on the basis of the photochromic h-fused benzo[f]chromene compounds according to the invention, any compatible dyeings (tolerated well from a chemical standpoint and with regard to the color), i.e., dyes may be applied to or embedded in the synthetic resin material to comply with aesthetic factors as well as medical or fashion aspects. The dye(s) selected specifically may consequently vary, depending on the intended effects and requirements.

The photochromic h-fused benzo[f]chromene compounds according to the invention with the general formulas (I) and/or (II), (III) and (IV) can be synthesized by reaction of suitably substituted fused 2-naphthol compounds with suitably substituted 2-propyn-1-ol compounds in a known way (see WO 02/22594). Production of the inventive compounds is explained below on the basis of a general reaction scheme, which is illustrated in FIG. 1.

Suitably substituted aromatic Grignard compounds having a protected acetic acid function in the ortho position are added to cyclic aromatic aliphatic ketones (step i). After eliminating water and removing the carboxylic acid protective group, substituted fused 2-naphthol compounds (steps ii and iii) are formed via intramolecular cyclization. These 2-naphthol compounds are then reacted with suitably substituted 2-propyn-1-ol compounds according to step iv) to form the compounds according to the invention.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A photochromic h-fused benzo[f]chromene compound corresponding to formula I:

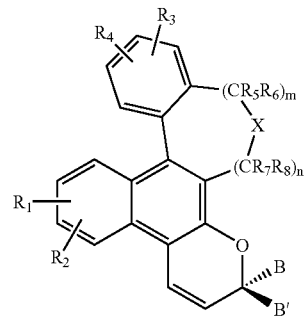

wherein
- n and m independently of one another denote 0, 1 or 2;
- $R_1$, $R_2$, $R_3$ and $R_4$ each independently of one another denote a substituent selected from
  - the group α consisting of a hydrogen atom, a ($C_1$-$C_6$) alkyl radical, a ($C_1$-$C_6$) thioalkyl radical, a ($C_3$-$C_7$) cycloalkyl radical which may include one or more heteroatoms, a ($C_1$-$C_6$) alkoxy radical, a hydroxyl group, a trifluoromethyl group, bromine, chlorine and fluorine; or the group β consisting of an unsubstituted, monosubstituted or disubstituted phenyl, phenoxy, benzyl, benzyloxy, naphthyl or naphthoxy group, wherein the substituents are selected from phenyl and the group α; or
  - the group γ wherein $R_1$ and $R_2$, or $R_3$ and $R_4$, or both $R_1$ and $R_2$, or $R_3$ and $R_4$ each denote an -A-$(CH_2)_k$-D- group or an -A-$(C(CH_3)_2)_k$-D- group bound to the aromatic ring, wherein k=1 or 2, wherein A and D are independently selected from the group consisting of oxygen, sulfur, $CH_2$, $C(CH_3)_2$ and $C(C_6H_5)_2$, and wherein a benzo ring optionally may be fused to the -A-$(CH_2)_k$-D- group;
- $R_5$, $R_6$, $R_7$ and $R_8$ each independently of one another are selected from phenyl and the group α, or
- $R_5$ and $R_6$ together with the $R_3$ group of the directly vicinal benzo ring form an unsubstituted, monosubstituted or disubstituted benzo or pyrido ring fused thereto, its substituents being selected from phenyl and the group α, or
- if m or n is 2, the directly vicinal $R_5$ and $R_6$ groups of two vicinal $CR_5R_6$ units or the directly vicinal $R_7$ and $R_8$ groups of two vicinal $CR_7R_8$ units together form a fused, unsubstituted, monosubstituted or disubstituted benzo ring or pyrido ring wherein any substituents are selected from phenyl and group α, or
- $R_5$ and $R_6$, or $R_7$ and $R_8$, or both $R_5$ and $R_6$ and $R_7$ and $R_8$, together form a ($C_3$-$C_7$) cycloalkyl group which may contain one or more heteroatoms selected from oxygen and sulfur, with a benzo ring optionally being fused to this cycloalkyl group;
- X is selected from O, S or $CR_9R_{10}$, wherein $R_9$ and $R_{10}$ independently of one another are selected from phenyl and the group α, or $R_9$ and $R_{10}$ together form a ($C_3$-$C_7$) cycloalkyl group which may contain one or more heteroatoms, or $R_9$ and $R_{10}$ together with $R_5$ and $R_6$ and/or $R_7$ and $R_8$ of a directly vicinal $CR_5R_6$ unit or $CR_7R_8$ unit or both may represent an unsubstituted, a monosubstituted or a disubstituted benzo ring or pyrido ring fused to the X—C($R_5R_6$) or X—C($R_7R_8$) bond, wherein any substituents are selected from phenyl and the group α, with the proviso that X is not $CR_9R_{10}$ when both m and n are 0;
- B and B' independently of one another are selected from the groups a), b), c) and d) consisting of:
  - a) mono-, di- and trisubstituted aryl groups selected from phenyl and naphthyl;
  - b) unsubstituted, monosubstituted and disubstituted heteroaryl groups selected from pyridyl, furanyl, benzofuran-2-yl, benzofuran-3-yl, dibenzofuranyl, thienyl, benzothien-2-yl, benzothien-3-yl and dibenzothienyl;
    - wherein any substituents of the aryl or heteroaryl groups in a) or b) are selected from the groups α, β and γ, an unsubstituted, monosubstituted or disubstituted amino group,
    - wherein the amine substituents are selected from the group consisting of ($C_1$-$C_6$) alkyl, ($C_3$-$C_7$) cycloalkyl, unsubstituted phenyl or benzyl, and phenyl or benzyl substituted with one or more substituents selected from the group α,
    - an N-morpholine group, an N-thiomorpholine group, an N-Pepperdine group, an N-azacycloheptane group, an N-piperazine group, an N-(N'-($C_1$-$C_6$-alkyl)piperazine group, an N-pyrrolidine group, an N-imidazolidine group, an N-pyrazolidine group, an N-aziridine group, an N-azetidine group, an N-indoline group, an N-carbazole group, an N-phenothiazine group, an N-phenazine group, an N-phenoxazine group, an N-tetrahydroquinoline group or an N-tetrahydroisoquinoline group;
  - c) structural units corresponding to formula (V) or formula (W):

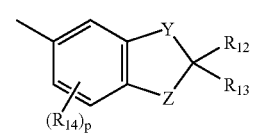

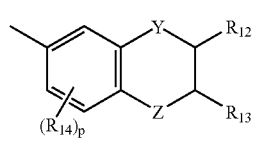

wherein
  - Y and Z independently of one another denote O, S, $CH_2$, $CMe_2$, NH, NPh or N($C_1$-$C_6$) alkyl;
  - $R_{12}$ and $R_{13}$ independently of one another denote hydrogen or ($C_1$-$C_6$)-alkyl, and
  - $R_{14}$ denotes a substituent from the group α, where p is 1, 2 or 3;
  - d) B and B' together form an unsubstituted, monosubstituted or disubstituted 9,10-dihydroanthracene group, fluorene group, thioxanthene group or xanthen-9-ylidene group, benzo[b]flouren-11ylidene group, 5H-dibenzo[a,c]cycloheptene, dibenzosuberone or 5H-dibenzo[a,c]cyclooctan-5-ylidene group or a saturated hydrocarbon group which is $C_3$-$C_{12}$ spiromonocyclic, $C_7$-$C_{12}$ spirobicyclic or $C_7$-$C_{12}$ spirotricyclic, wherein any substituents on the unsaturated cyclic compounds are selected from the group α.

2. A photochromic benzo[f]chromene compound as claimed in claim 1, wherein the cyclic ring or heterocyclic ring fused in h-position of the benzo[f]chromene system according to formula (I) is a five-membered ring, a six-membered ring or a seven-membered ring.

3. A photochromic benzo[f]chromene compound as claimed in claim 1, wherein said compound corresponds to formula (II), (III) or (IV):

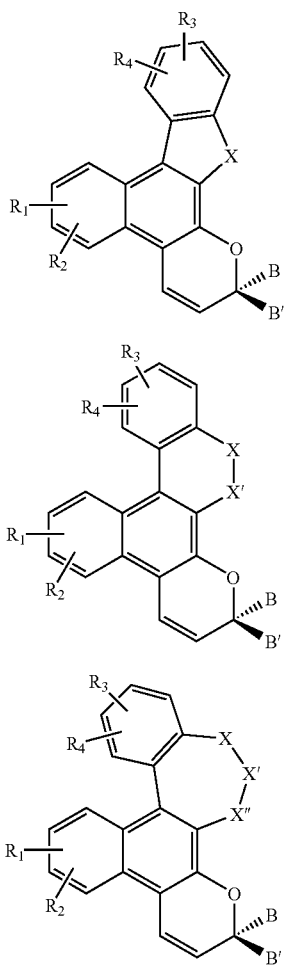

wherein
in formula (II) X denotes O or S;
in formula (III) X and X' independently of one another are selected from O, S or $CR_9R_{10}$, with the proviso that at least one of X and X' is $CR_9R_{10}$;
in formula (IV) X, X' and X" are independently selected from O, S and $CR_9R_{10}$, with the proviso that when X' denotes O or S, then X and X" each denote $CR_9R_{10}$.

4. A photochromic benzo[f]chromene compound as claimed in claim 1, wherein $R_1$, $R_2$, $R_3$ and $R_4$ are each selected from the groups α and β.

5. A photochromic benzo[f]chromene compound as claimed in claim 1, wherein $R_5$, $R_6$, $R_7$ and $R_8$ are each independently selected from the group α.

6. A photochromic benzo[f]chromene compound as claimed in claim 1, wherein B and B' each independently denote a mono-, di- or trisubstituted aryl group selected from phenyl and naphthyl.

7. A photochromic benzo[f]chromene compound as claimed in claim 1, selected from the group consisting of:
2-(4-methoxyphenyl)-2-phenyl-2H-benzofurano[1,2-h]benzo[f]chromene;
2-(4-methoxyphenyl)-2-phenyl-2H-benzothiopheno[1,2-h]benzo[f]chromene;
2-(4-methoxyphenyl)-2-phenyl-2H-13,14-dihydronaphtho [1,2-h]benzo[f]-chromene;
7-methoxy-2-(4-methoxyphenyl)-2-phenyl-2H-13,14-dihydronaphtho [1,2-h]-benzo[f]chromene;
11-methoxy-2-(4-methoxyphenyl)-2-phenyl-2H-13,14-dihydronaphtho[1,2-h]benzo[f]chromene;
2-(4-methoxyphenyl)-2-phenyl-2H,13H-chromeno [1,2-h]benzo [f]chromene;
2-(4-methoxyphenyl)-2-phenyl-2H,14H-chromeno [1,2-h]benzo [f]chromene; and
7-methoxy-2-(4-methoxyphenyl)-2-phenyl-2H-benzocycloheptano[1,2-h]-benzo[f]chromene.

8. A photochromic synthetic resin article comprising a photochromic benzo[f]chromene compound as claimed in claim 1.

9. An article as claimed in claim 8, wherein said article is an ophthalmic lens.

* * * * *